US010550360B2

(12) United States Patent
Grosch et al.

(10) Patent No.: US 10,550,360 B2
(45) Date of Patent: Feb. 4, 2020

(54) FLUID SUPPLY INTERFACE, IN PARTICULAR FOR SUPPLYING CELL CULTURE CONTAINERS, COMPRISING FLUID CHANNELS VARIABLY CONNECTABLE TO THE FLUID LINE

(71) Applicant: Hamilton Bonaduz AG, Bonaduz (CH)

(72) Inventors: Jens Grosch, Basel (CH); Tom Kissling, Riehen (CH); Thomas Zumstein, Weil am Rhein (DE)

(73) Assignee: Hamilton Bonaduz AG, Bonaduz (CH)

( * ) Notice: Subject to any disclaimer, the term of this patent is extended or adjusted under 35 U.S.C. 154(b) by 315 days.

(21) Appl. No.: 15/536,764

(22) PCT Filed: Dec. 4, 2015

(86) PCT No.: PCT/EP2015/078717
§ 371 (c)(1),
(2) Date: Jun. 16, 2017

(87) PCT Pub. No.: WO2016/096489
PCT Pub. Date: Jun. 23, 2016

(65) Prior Publication Data
US 2017/0342364 A1 Nov. 30, 2017

(30) Foreign Application Priority Data
Dec. 19, 2014 (DE) .................. 10 2014 226 692

(51) Int. Cl.
*C12M 1/24* (2006.01)
*C12M 1/00* (2006.01)
*B01L 3/00* (2006.01)

(52) U.S. Cl.
CPC .............. *C12M 23/40* (2013.01); *B01L 3/563* (2013.01); *C12M 23/08* (2013.01)

(58) Field of Classification Search
CPC ......... C12M 23/08; C12M 23/40; B01L 3/563
See application file for complete search history.

(56) References Cited

U.S. PATENT DOCUMENTS

| 5,350,080 A | 9/1994 | Brown et al. |
| 2009/0111180 A1 | 4/2009 | Vilendrer |
| | (Continued) | |

FOREIGN PATENT DOCUMENTS

| DE | 4207346 | 9/1993 |
| DE | 102004045785 | 5/2006 |
| | (Continued) | |

OTHER PUBLICATIONS

International Search Report filed in PCT/EP2015/078717 dated Mar. 23, 2016.
German Search Report filed in 102014226692.0 dated May 11, 2015.

*Primary Examiner* — William H. Beisner
(74) *Attorney, Agent, or Firm* — Rankin, Hill & Clark LLP

(57) ABSTRACT

A fluid supply interface includes a line component having a first coupling formation for the temporary coupling of a first fluid channel, a second coupling formation for the temporary coupling of a second fluid channel, and a third coupling formation for the temporary or permanent coupling of a third fluid channel, each of said coupling formations being penetrated by a fluid line section, wherein in the line component, a fluid line assembly is formed, by means of which each fluid line section of the first, second and third coupling formations is or can be connected to each fluid line section of the other two coupling formations for the purpose of fluid transport.

16 Claims, 7 Drawing Sheets

(56) References Cited

U.S. PATENT DOCUMENTS

Figure 1:
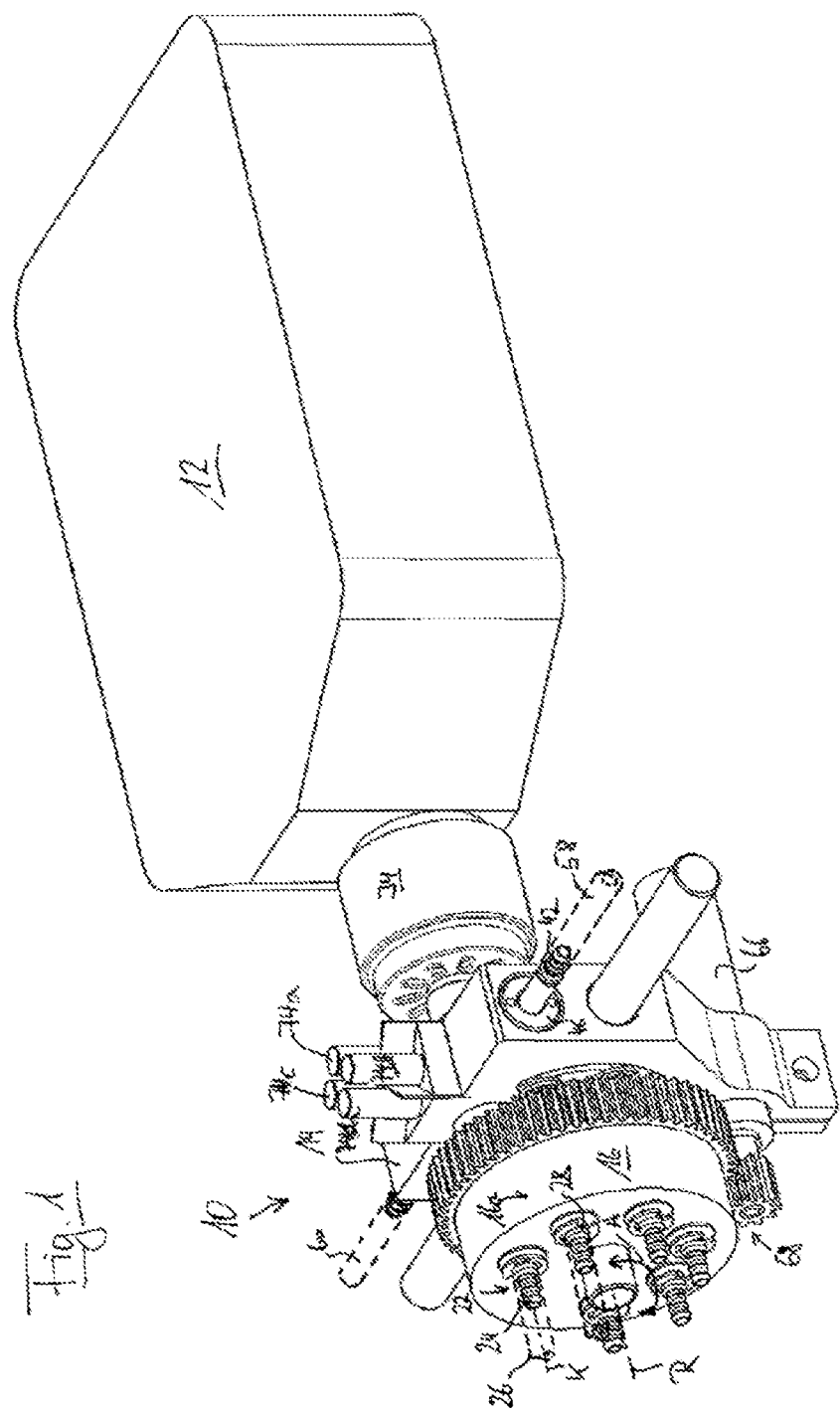

2011/0223076 A1    9/2011  Wynn
2014/0076454 A1    3/2014  Kjar

FOREIGN PATENT DOCUMENTS

| EP | 1672265 | 6/2006 |
|----|---------|--------|
| GB | 2433304 | 6/2007 |
| WO | 2009/069960 | 6/2009 |
| WO | 2011090781 | 7/2011 |
| WO | 2012088014 | 6/2012 |
| WO | 2014114610 | 7/2014 |

FLUID SUPPLY INTERFACE, IN PARTICULAR FOR SUPPLYING CELL CULTURE CONTAINERS, COMPRISING FLUID CHANNELS VARIABLY CONNECTABLE TO THE FLUID LINE

The present invention relates to a fluid supply interface, in particular for a cell culture system, for introducing a fluid into a cell culture container or/and for draining a fluid therefrom, comprising a line component having a first coupling formation for the temporary coupling of a first fluid channel, preferably a fluid channel of a cell culture container, and having a second coupling formation for the temporary coupling of a second fluid channel, preferably a fluid channel of a fluid reservoir, and having a third coupling formation for the temporary or permanent coupling of a third fluid channel, preferably a waste removal channel, each of said coupling formations being penetrated by a fluid line section, wherein a fluid line assembly is formed in the line component, via which each fluid line section of the first, second and third coupling formations is or can be connected to each fluid line section of the other two coupling formations for the purpose of fluid transport.

A fluid supply interface of this type is known from WO 2014/114610 A. Said document shows a fluid supply interface of the type in question, specifically in its FIGS. 2 and 3.

Although excellent results are achieved with the known fluid supply interface, which can be used to manipulate the fluid balance of a plurality of cell culture containers or other objects that can be fluidically connected to said interface, there is still room for improvement even of this known fluid supply interface.

The advantage of the fluid supply interfaces in question is that a single fluid supply interface can be connected to a plurality of different containers, for example to a plurality of cell culture containers, so that a single fluid supply interface can be used to introduce fluid into the connected containers, drain fluid from said containers for disposal, and where appropriate, remove product from the connectable containers via the fluid supply interface, hence different cell culture containers can be "harvested" using one and the same fluid supply interface. Since a cleaning fluid reservoir may also be coupled to the coupling formations provided on the fluid supply interface for the coupling of fluid channels, sufficient capability for cleaning the fluid line assembly provided in the fluid supply interface is provided to overcome any fear of contamination, in particular highly dangerous cross-contamination, despite the 1:n ratio of the fluid supply interface to a plurality of cell culture containers.

One aspect of the known fluid supply interface that is worthy of improvement is its installation space requirement. As the number of coupling formations and fluid channels coupled thereto increases, the amount of installation space required by the known fluid supply interface increases.

It is therefore the object of the present invention to improve the fluid supply interface described at the outset in terms of its installation space requirement, so that it takes up less installation space than the known fluid supply interface with the same number of coupled or coupleable fluid channels.

This object is achieved according to the invention by a fluid supply interface of the type in question as described at the outset, in which the fluid supply interface additionally has a fluid channel base, which is movable relative to the line part and which has at least two fluid channel base connector formations, which are configured as separate from one another and are connected to different fluid channels for fluid transport, each said connector formation being penetrated by a fluid channel section, and in which one of the three coupling formations is embodied as a switchable coupling formation for the temporary production of a common fluid line segment with a fluid channel base connector formation that can be selected by a relative movement of the line component and the fluid channel base.

In contrast to the known fluid supply interface of the type in question, in which all fluid channels that are coupled thereto—with the exception of the cell culture container fluid channels, which are intended to be coupled only temporarily—are fixedly connected to the fluid supply interface, in the fluid supply interface according to the invention, in addition to the coupling formation for the cell culture container, at least one additional coupling formation is configured as a switchable coupling formation with which a fluid channel forms a common fluid line segment only temporarily.

For this purpose, the fluid channel base has at least two fluid channel base connector formations, which are embodied as separate from one another and are connected to different fluid channels for the purpose of fluid transport, each such connector formation being temporarily coupleable to the switchable coupling formation of the line component to produce a common fluid line segment. The fluid channel base connector formation that will form a common fluid line segment with the switchable coupling formation of the line component can be selected in a simple manner by a relative movement of the fluid channel base and the line part. Thus, with the fluid supply interface according to the invention, a greater number of fluid channels leading to and/or away from said fluid supply interface can advantageously be permanently connected to it than coupling formations are provided on the line component. The number of coupling formations on the line component can therefore be decreased, leading to the desired savings of installation space.

Although fluid channels are fixedly connected to the fluid supply interface according to the invention via the fluid channel base, they are not fixedly connected to the switchable coupling formation of the line component.

The selection of a fluid channel base connector formation as the coupling connector formation that will form a common fluid line segment with the switchable coupling formation can be made structurally in a simple manner in that the fluid channel base has at least two relative operating positions, in each of which a different fluid channel base connector formation is selected as the coupling connector formation, and the switchable coupling formation is in closer proximity than the respectively other fluid channel base connector formation.

The movement toward the selected coupling connector formation is generally understood as being carried out by the fluid channel base and the movement toward the switchable coupling formation is generally understood as being carried out by the line component. The state in which the coupling connector formation is in closer proximity to the switchable coupling formation can be a coupling ready position, for example, in which the coupling connector formation is then located. In this coupling ready position, the fluid channel section that penetrates the coupling connector formation and the fluid line section that penetrates the switchable coupling formation are preferably aligned with one another, so that proceeding from this coupling ready position, an actual ability to conduct fluid through the designated sections: fluid channel section and fluid line section, can be produced easily and quickly.

Alternatively or additionally, when the coupling connector formation is in a state of closer proximity to the switchable coupling formation, it can be located in a coupling position, in which the fluid channel section that penetrates the coupling connector formation and the fluid line section that penetrates the switchable coupling formation are coupled to form a common fluid line segment that penetrates the coupling connector formation and the switchable coupling formation. In this case, the common fluid line segment, in which the involved sections: fluid channel section, fluid line section, coupling connector formation and switchable coupling formation participate, is already produced.

Although in principle it is conceivable for the switchable coupling formation to be provided movably on the line component, and for the movability thus created to be used to produce a common fluid line segment between coupling connector formation and switchable coupling formation, it is preferable for the movability to be provided in the coupling connector formation. It is therefore preferable for the respective coupling connector formation to be displaceable between the coupling ready position and the coupling position. This displaceability is preferably a displaceability relative to the fluid channel base, on which the coupling connector formation is held as the fluid channel base connector formation, and also relative to the line component, on which the switchable coupling formation is located. In that case, when the fluid channel section that penetrates the coupling connector formation and the fluid line section that penetrates the switchable coupling formation are aligned with one another in the coupling ready position, the selected coupling connector formation in each case can preferably be displaceable to the coupling position and back again without changing the relative position of fluid channel base and line component.

The displacement of the coupling connector formation between the coupling ready position and the coupling position relative to the fluid channel base is preferably carried out along a coupling path that, for the easiest possible displacement, can be a preferably partially, and particularly preferably fully straight-line coupling axis.

Furthermore, the fluid channel base connector formations, including the coupling connector formation selected for coupling to the switchable coupling formation, can be moved together with the fluid channel base relative to the line component along a selection path. The selection path is defined by a guide means that guides the relative movement of fluid channel base and line component for the selection of a fluid channel base connector formation as the coupling connector formation.

To prevent any confusion between the two movement paths, coupling path and selection path are different from one another, so that an operator initiating the respective movements can clearly distinguish between the selection of a fluid channel base connector formation as the coupling connector formation and the production of a common fluid line segment of the coupling connector formation and the switchable coupling formation.

The coupling path and the selection path are preferably oriented orthogonally to one another so that, wherever possible, movement along one of the paths has no movement component along the respectively other path. Orthogonal movements in the context of the present application are not only translational movements having mutually orthogonal translational directions of movement, but also rotational movements about mutually orthogonal rotational axes, and a translational movement along a movement axis and a rotational movement about a rotational axis that is parallel to or collinear with the movement axis. This list is expressly incomplete, so that further configurations of translational and rotational movement can lead to mutually orthogonal movement paths.

To make the fluid supply interface of the invention as easy for a user to operate as possible, the fluid supply interface can have a power unit by means of which the coupling connector formation can be displaced from the coupling ready position to the coupling position and/or vice versa. Said power unit performs tasks that would otherwise have to be performed manually by the operator. Moreover, the power unit can supply a repeatable displacement force that ensures successful coupling between the coupling connector formation and the switchable coupling formation with sufficient certainty. Suitable power units include electromotive drives, electromagnets, and pneumatic or hydraulic drives. The power unit is preferably an electromagnetic drive, optionally with a gearing mechanism interposed.

The power unit can be designed to supply sufficient coupling force to couple the coupling connector formation to the switchable coupling formation in a fluid-tight connection, for the entire time during which the common fluid line segment is being produced. To achieve a preferred energy savings, however, according to an advantageous refinement of the present invention the coupling connector formation may be locked in the coupling position relative to the line component and thus generally also relative to the fluid channel base. This advantageous refinement of a locking mechanism can be implemented independently of the above-described provision of the power unit.

To provide a defined starting position and to simplify the structure of the power unit, the coupling connector formation or each fluid channel base connector formation can be displaceable in a direction opposite the prestressing force of a prestressing device between the coupling ready position and the coupling position. In this case, the power unit needs to apply force in only one direction, while it can be reset in the opposite direction by the prestressing device. The prestressing device can be a spring.

The fluid line assembly can connect the fluid line sections of the first, second and third coupling formations of the line component in parallel, in other words, two coupling formations are connected to one another by the fluid line assembly in such a way that other coupling formations are substantially bypassed by the paired connection of two coupling formations. A preferred parallel connection of the first, second and third coupling formations produces a radial configuration of the fluid line assembly.

Alternatively, the fluid line assembly can also connect the fluid line sections of the first, second and third coupling formations to one another in series. This means that under certain circumstances, a target connector formation is reached by a fluid flow proceeding from a starting connector formation only after the fluid flow has passed a further connector formation located between the starting and the target connector formation. The series connection is preferably configured in the line component as arcuate or polygonal and is particularly preferably ring-shaped, that is, in the shape of a closed ring. However, "ring-shaped" does not necessarily mean an arcuate or even a circular ring-shaped profile. A ring-shaped profile can also be achieved by juxtaposing rectilinear line sections, provided these are joined to form a closed-circumferential line.

To prevent a valve body, which for long operating intervals blocks a fluid line section that penetrates a coupling formation, preventing the passage of fluid, from interfering with the fluid line when the fluid line is routed through the fluid line section that penetrates the coupling formation of the valve body, the fluid line assembly preferably has a receiving opening designed to temporarily receive the valve body in the region of at least one coupling formation. Said receiving opening can preferably be provided in a space-saving manner in a direction orthogonally to the opening area of a mouth of the fluid line section that penetrates the coupling formation, offset into the line component in the at least one coupling formation. This can be achieved easily in structural terms particularly when the coupling formations are connected in series.

In the case of the parallel, preferably radial configuration of the fluid line assembly, the receiving opening can be provided laterally on the fluid line section, so that the valve body can be moved into and back out of the receiving opening orthogonally or at least with a movement component that is orthogonal to the fluid line section that penetrates the respective coupling formation.

To enable the valve body, which can also be exposed in the receiving opening to the forces of a stream of fluid flowing past it, to be held as securely as possible in the receiving opening, it is preferred according to an advantageous refinement of the invention for the receiving opening to be configured as at least partially complementary to a surface section of the valve body.

To dispense with any considerations regarding the orientation of the valve body, the valve body is preferably a valve ball, in which case the receiving opening can preferably be configured as concave/partly spherical.

To achieve the most fluid-tight coupling of a coupling formation to a connector formation, it can be provided according to a preferred refinement that the mouth of the fluid line section is encompassed at the switchable coupling formation, and preferably also at least at one additional coupling formation, by a seal or by a contact surface, preferably by a planar contact surface, which is designed for the placement thereon of a seal provided on a connector formation.

Furthermore, in particular in the aforementioned preferred application example of the fluid supply interface in a cell culture system, described herein, that is to say designed to coordinate with a cell culture container, a fixed connection of coupling formation and connector formation may be desirable. For that reason, at least one of the coupling formations may be permanently coupled to a connector formation to form a common fluid line segment that penetrates the connector formation and the coupling formation. This may be advantageous for a fluid channel that leads to a waste container, for example, since the connection to the waste container, or generally to a fluid sink, may always be required.

A further advantage of the fixed arrangement of at least one fluid channel or the connector formation thereof to a coupling formation of the line component may be that the permanent coupling can provide a fluid line section that bypasses the fluid line section at the switchable coupling formation. This is also advantageous for the disposal of waste fluid, for example, so that waste fluid does not need to be conducted through the fluid line section of the switchable coupling formation, through which sterile culture fluid may later be conducted back into the cell culture container. It should be expressly noted that in testing, the present fluid supply interface could be cleaned well enough by flushing it with cleaning fluid that common fluid line sections could easily be used without problems for the passage of both waste fluid and nutrient fluid. Separating these fluid conducting paths thus merely increases the operational safety of the fluid supply interface, which is adequate as it is.

Reference has already been made above to a valve body. The various coupling formations provided on the line component and the fluid line assembly that connects said formations are intended to produce different fluid line sections in order to increase the level of operating hygiene that can be achieved for different fluids using the present fluid supply interface. This can be advantageously accomplished in that a connector formation that can be or is coupled to a coupling formation to form a common fluid line segment has a valve seat and a valve body, which rests on the valve seat in an operating mode in which the fluid channel section of the connector formation is blocked for fluid passage.

The valve seat can advantageously have a magnet with which the valve body, which is preferably at least partially or even entirely made of ferromagnetic material, can be prestressed into a blocking position in which the valve body rests on the valve seat. For the most homogeneous distribution of force possible during the prestressing of the valve body toward the valve seat, it may be advantageous to use a ring-shaped magnet, with the ring axis that penetrates the ring orthogonally to a ring plane in which the ring extends more preferably advantageously coinciding with the orientation of the fluid channel section that penetrates the connector formation in question, i.e. is preferably collinear therewith.

Fluid can preferably flow through the magnet that prestresses the valve body in the closed position, so that it can be provided in or near the connector formation that comprises the valve seat, occupying minimal installation space.

However, since it is not necessary to permanently block all possible fluid line sections, it is conceivable for one or more valve bodies to be used jointly by a plurality of coupling formations. This can be enabled structurally, for example, by designing the dimensions of at least one displacement section of the fluid line assembly that proceeds from the coupling formation and extends in the direction of a further coupling formation such that said displacement section permits a displacement of the valve body away from the coupling formation, preferably up to another coupling formation, and back.

A particularly advantageous option for switching the valve bodies without contact and therefore highly hygienically between two positions, in one of which the valve body blocks the passage of fluid through the valve seat and in the other permits the passage of fluid through the valve seat, can be achieved in that the valve body contains ferromagnetic material, in particular is made of ferromagnetic material, and in that the fluid supply interface is equipped with a magnetic switching device having a magnetic field strength that is locally variable at the coupling formations, and with which the valve body can be released from the valve seat.

The various relative movement paths, specifically the selection path and the coupling path, have already been described above. With regard to the object to be achieved, specifically the provision of the present fluid supply interface with decreased installation space as compared with the prior art, it is preferable for the fluid channel base to be rotatable relative to the line component about a rotational axis, preferably about a rotational axis that is parallel to the orientation of the fluid line section that penetrates the switchable coupling formation, or to be displaceable relative to the line component along a translational axis, preferably along a translational axis that is orthogonal to the orientation of the fluid line section that penetrates the switchable coupling formation. Since the fluid supply interface discussed herein can be advantageously used above all in cell culture systems that have at least one cell culture container, the present invention also relates to a cell culture system having at least one cell culture container, at least two separate fluid reservoirs, a fluid disposal sink and a fluid supply interface as described above and optionally as refined, wherein the cell culture container comprises a connector formation, wherein the coupling connections of the fluid channel base are fluidically connected to the fluid reservoirs, and wherein the first coupling formation of the line component is configured to produce a temporary fluid transport connection with the cell culture container connector formation, the second coupling formation of the line component is configured as the switchable coupling formation to produce a temporary fluid transport connection with one of the fluid channel base connector formations, and the third coupling formation of the line component is configured to produce a temporary or permanent fluid transport connection with the fluid disposal sink.

The cell culture system preferably comprises a plurality of cell culture containers and a smaller number of fluid supply interfaces than the number of cell culture containers, preferably only one fluid supply interface.

The fluid channel base can have more than two fluid channel base connector formations, for example three, four, five, six or even more than six fluid channel base connector formations, in which: If more than three fluid channel base connector formations are provided, a rotational relative mobility of the fluid channel base relative to the line component requires less space for installation and movement than a translational relative mobility. The fluid channel base connector formations with the fluid channel sections that penetrate them are preferably provided parallel to the relative rotational axis of the fluid channel base relative to the line component with a radially equal distance from the relative rotational axis.

The fluid channel base itself can in turn be motorized for relative movement along the selection path. For this purpose, the fluid supply interface can have a movement drive, which can be provided on the line component or on a component that is fixedly coupled to the line component, such as a frame or the like, coupled to the fluid channel base so as to transmit movement and force.

Figure 2:
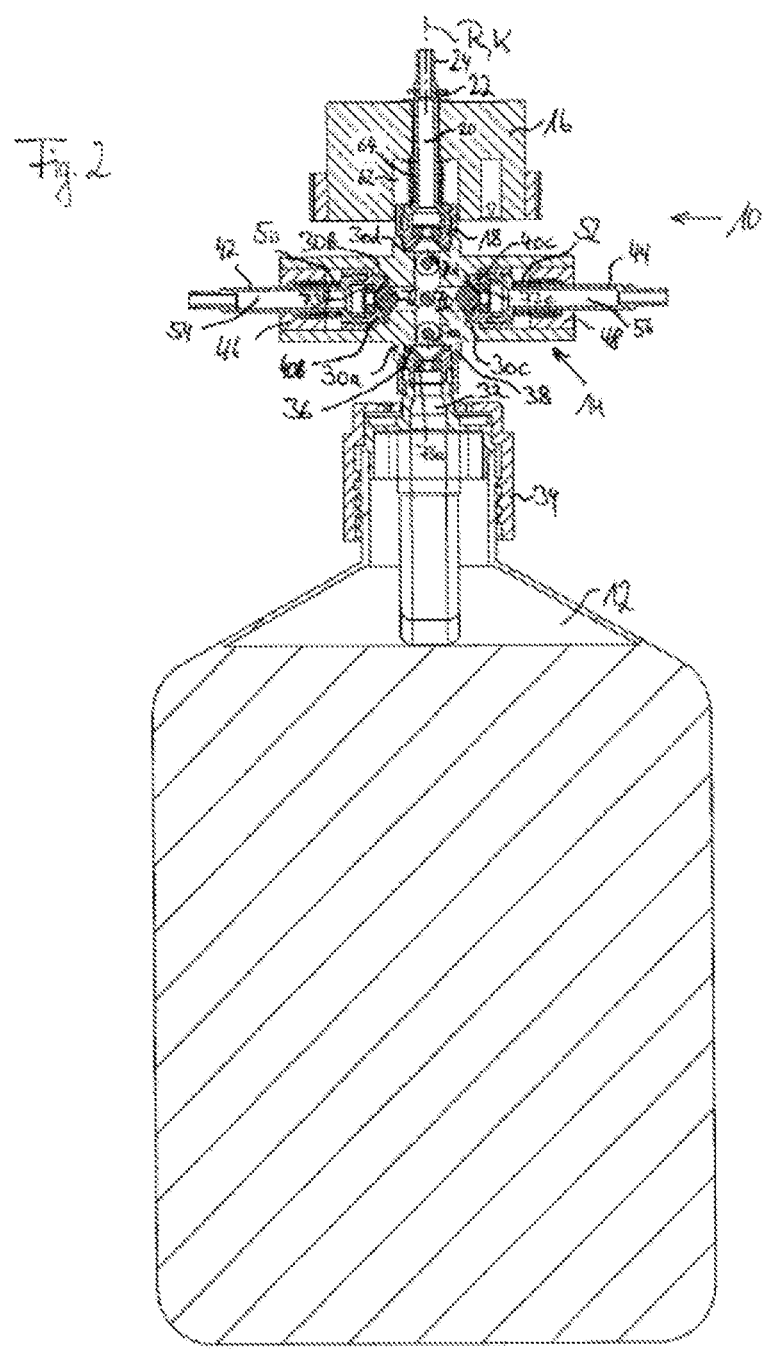
Figure 3:
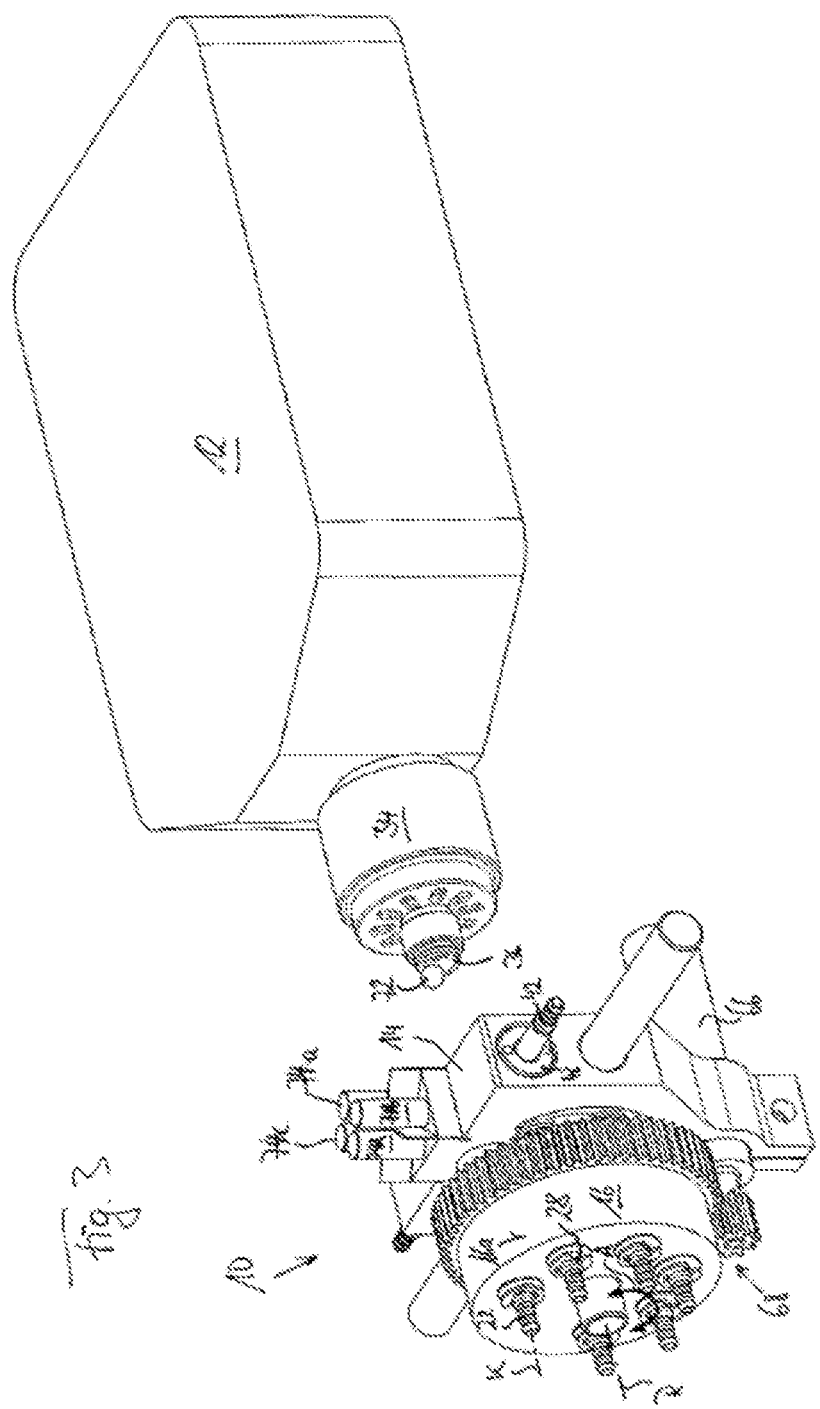
Figure 4:
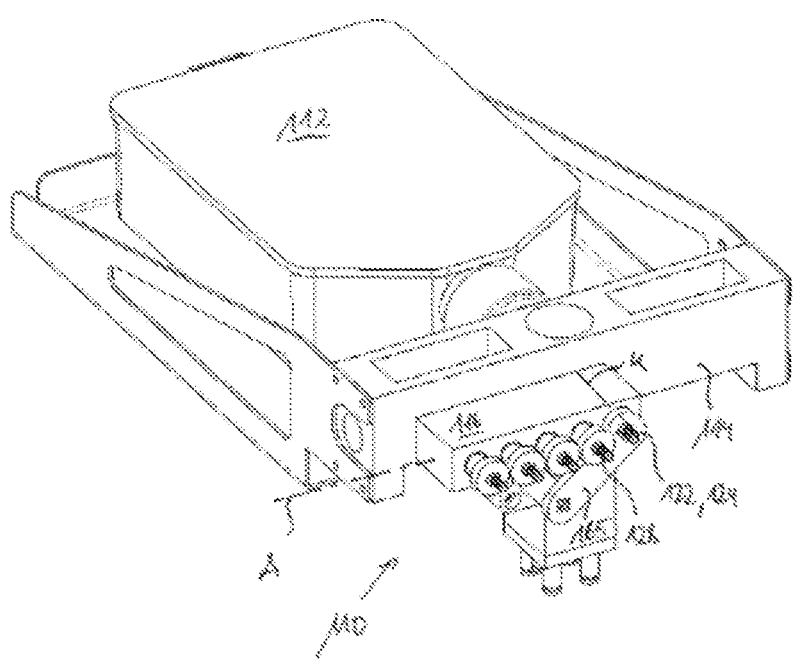
Figure 5:
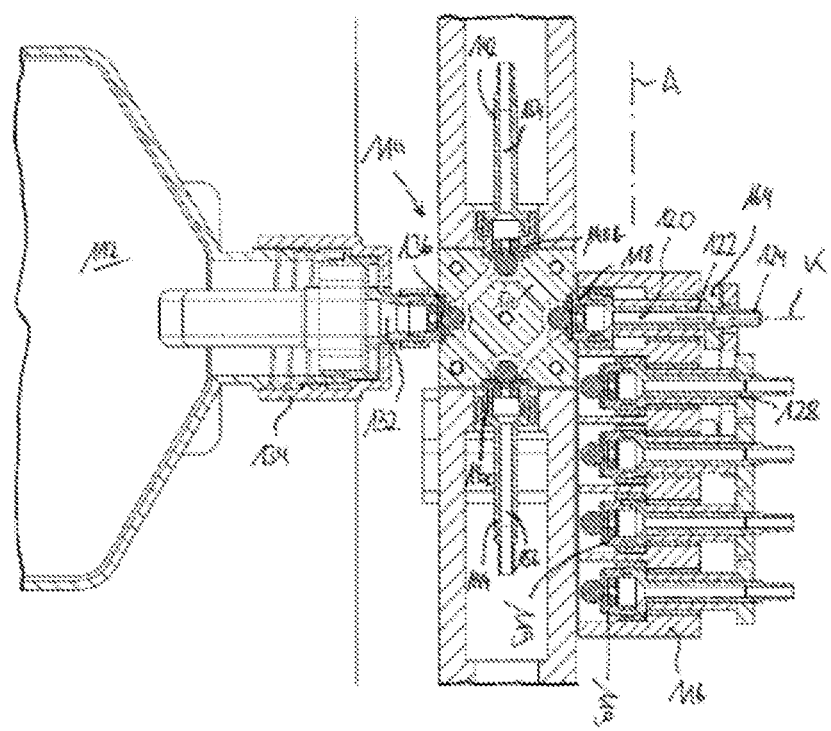
Figure 6:
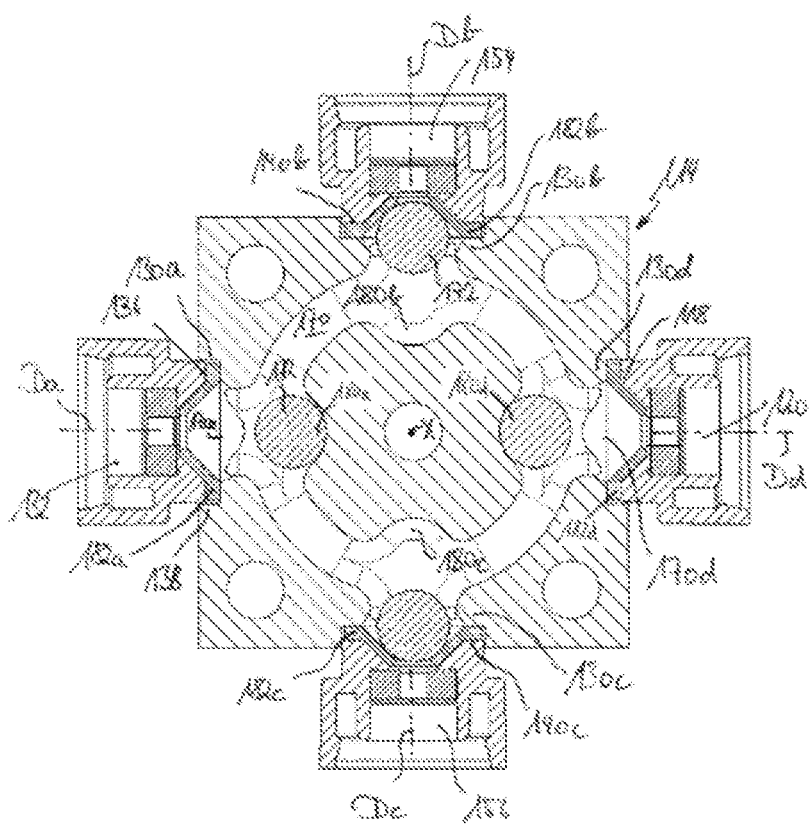
Figure 7:
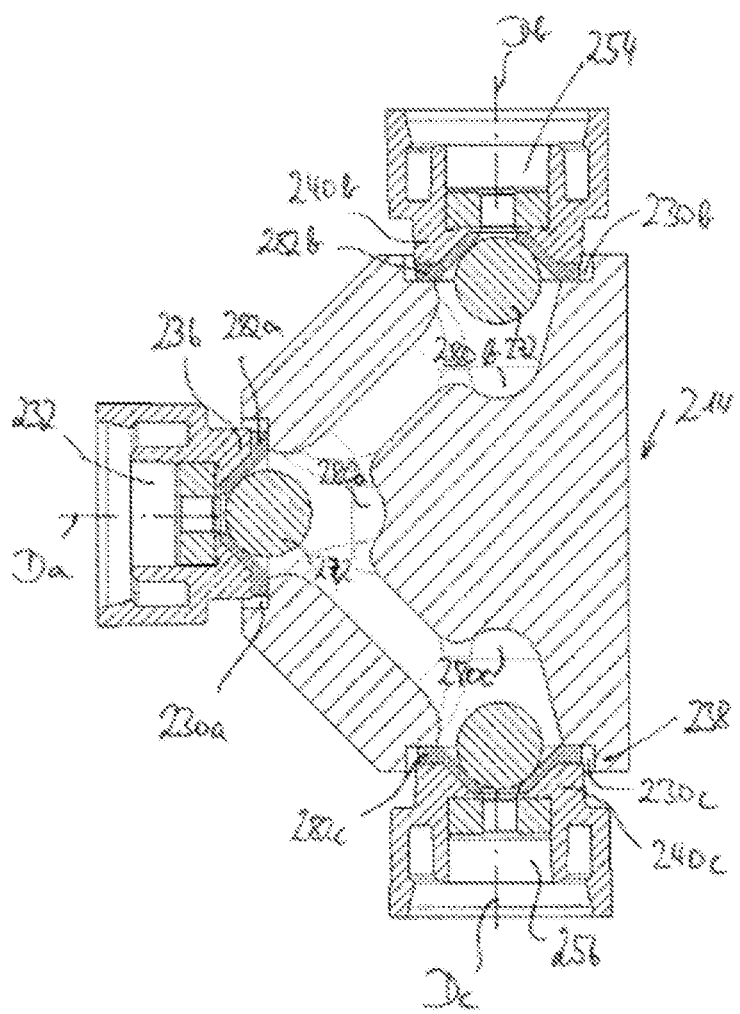

The present invention will be explained in greater detail in the following, with reference to the appended drawings. The drawings show:

FIG. 1 a first embodiment of a fluid supply interface according to the invention, with a cell culture container connected thereto, from a perspective view, FIG. 2 a longitudinal section of the embodiment of FIG. 1, FIG. 3 the first embodiment of FIG. 1 with the cell culture container uncoupled, FIG. 4 a second embodiment of a fluid supply interface according to the invention with the cell culture container coupled, FIG. 5 a longitudinal sectional view of the second embodiment of FIG. 4, FIG. 6 a detail view of the line component of the fluid supply interface of FIG. 5 and FIG. 7 an alternative line component for the second embodiment.

In FIG. 1, a first embodiment of a fluid supply interface of the present invention is generally labeled as 10. A cell culture container 12 is coupled to this fluid supply interface 10 in FIGS. 1 and 2.

Fluid supply interface 10 comprises a line component 14, on which a fluid channel base 16 is provided so as to rotate about a rotational axis R.

On fluid channel base 16, a plurality of fluid channel base connector formations 18 (see FIG. 2)—in the present example precisely six—are held, with a fluid channel section 20 penetrating each.

Fluid channel base connector formation 18, like the remaining fluid channel base connector formations 19 (see "119" in FIG. 5), is formed on a fluid channel base connecting port 22, which is configured at its longitudinal end 24 that is distant from the fluid channel base connector formation 18 for the connection of a fluid conducting means 26, for example in the form of a flexible tube.

In FIGS. 1 and 3, a further connecting port is labeled as 28, to distinguish the fluid channel base connecting ports 22 from one another. The fluid channel base connecting ports are preferably substantially identical in configuration.

As is clear from FIG. 2, line component 14 has a plurality of coupling formations 30a to 30d—in the present example, four. Coupling formation 30a is configured for the temporary coupling of a fluid channel 32, which is provided in a known manner in a cap 34 of cell culture container 12. For coupling to the coupling formation 30a, cap 34 has a cell culture container connector formation 36, which is advantageously configured substantially in accordance with the remaining connector formations, for example fluid channel base connector formation 18.

Coupling formations 30a to 30d each preferably have a peripheral collar, into which the associated connector formation is inserted for coupling to the respective coupling formation 30a to 30d. For the sake of clarity, only collar 38 of coupling formation 30a is labeled with a reference symbol.

In the present example, coupling formations 30b and 30c are fixedly and permanently coupled to connector formations 40b and 40c to form a common fluid line segment. For this purpose, line component 14 can have support members 46 and 48, which are penetrated by fluid channel ports 42 and 44, respectively, and on which tension springs 50 and 52 are respectively supported, which prestress connector formations 40b and 40c, respectively, in relation to the respective coupling formations 30b and 30c. For this purpose, support members 46 and 48 are preferably fixedly connected to line component 14 as spring counter-bearings.

Connector formations 40b and 40c are penetrated by fluid channel sections 54 and 56, respectively, and are defined by connecting ports 42 and 44, which are each configured, in turn, at their longitudinal ends that are distant from connector formations 40b and 40c, respectively, for the attachment of one fluid conducting means each—in this case tubes 58 and 60, respectively.

In contrast to connector formations 40b and 40c, which are fixedly coupled to coupling formations 30b and 30c, coupling formation 30d can be coupled to different connector formations of fluid channel base 16 to produce a common fluid line segment. Coupling formation 30d will therefore hereinafter be referred to as switchable coupling formation 30d.

Since in FIGS. 1 to 3, the fluid channel base connector formation 18 of fluid channel base 16, which is visible only in FIG. 2, is in closest proximity to switchable coupling formation 30d, and has therefore been selected as coupling connector formation 18 for coupling to switchable coupling formation 30*d*, fluid channel base connector formation 18 will be referred to in the following as coupling connector formation 18. In FIG. 2, said connector formation is located in a coupling position, in which it is coupled to switchable coupling formation 30*d* to form a common fluid line segment, which then penetrates coupling connector formation 18 and switchable coupling formation 30*d*.

Coupling connector formation 18 of FIG. 2 can be shifted along a coupling path K, in particular coupling axis K, which is preferably parallel to rotational axis R, between the coupling position shown in FIG. 2 and a coupling ready position, in which coupling connector formation 18 is arranged at a distance from switchable coupling formation 30*d* along coupling path K. Coupling connector formation 18 is then located deeper in the coaxial receiving space 62 in the fluid channel base, so that fluid channel base 16 can be rotated about rotational axis R without fear of a collision between coupling connector formation 18 or another fluid channel base connector formation with switchable coupling formation 30*d*. In the coupling ready position, coupling connector formation 18 is preferably still aligned with switchable coupling formation 30*d*, so that coupling connector formation 18 can be transferred translationally into the coupling position in a simple manner by displacing the same along coupling path K up to switchable coupling formation 30*d*.

Like the other fluid channel base connector formations, coupling connector formation 18 can also be prestressed along coupling path K into the coupling position by a prestressing device, such as a helical spring 64. In this case, fluid channel base 16 has a power unit not shown in FIGS. 1 to 3, which pulls all the fluid channel base connector formations back against the force of the compression springs assigned to each of them into the receiving spaces likewise assigned to each of them. The fluid channel base connector formations or the connecting ports that support them can preferably be locked in the retracted position in fluid channel base 16, for example by a bayonet formation.

Alternatively, each of the fluid channel base connector formations can also be prestressed into its retracted position in the receiving space 62, for instance if helical spring 64 is a tension spring. In this case, at least the coupling connector formation 18 that is selected in each case for coupling to switchable coupling formation 30*d* can be shifted by means of a power unit not shown in FIGS. 1 to 3 against the force of prestressing spring 64 from the coupling ready position to the coupling position shown in FIG. 2, and can optionally be locked in the coupling position to prevent it from moving back into the coupling ready position.

One of the fluid channel base connector formations (see connecting ports 22 and 28 in FIGS. 1 and 3) can be selected as the coupling connector formation by rotating fluid channel base 16 relative to line component 14, in which the fluid channel base connector formation in question is moved along a circular path A as a selection path about rotational axis R until the selected coupling connector formation is aligned with switchable coupling formation 30*d* and is thus in a coupling ready position.

To facilitate movement of the fluid channel base connector formations about rotational axis R, a movement drive 66, particularly preferably an electromotive movement drive 66, is preferably provided on line component 14 and coupled to fluid channel base 16, for example via a gear train 68, so as to transmit movement and force. For this purpose, part of the outer circumferential surface 16*a* (cylindrical surface) of fluid channel base 16 can be embodied as a gear wheel or sprocket, preferably integrally by means of plastic injection molding.

In line component 14, a fluid line assembly 70 is provided, which fluidically interconnects fluid line sections 70*a* to 70*d*, which penetrate coupling formations 30*a* to 30*d*, respectively (for the sake of clarity, only fluid line sections 70*a* and 70*d* are labeled with reference symbols). Fluid line sections 70*b* and 70*c*, which are not specifically labeled, penetrate the coupling formations that are labeled with the same lower case letters, 30*b* and 30*c*, respectively.

In the example illustrated in FIG. 2, fluid line assembly 70 connects fluid line sections 70*a*, 70*b*, 70*c* and 70*d* parallel to one another in what is known as a radial configuration. In this embodiment, two of fluid line sections 70*a* to 70*d* can be fluidically connected to one another without the conduction of fluid having to flow along the remaining fluid line sections or past the coupling formations.

In FIG. 2, connector formations 40*b* and 40*c*, which are permanently coupled to coupling formations 30*b* and 30*c*, preferably support spherical valve bodies 72 (only valve body 72 at connector formation 40*d* is labeled with a reference symbol), which preferably comprise ferromagnetic material or are made of ferromagnetic material. In a known manner, line component 14 can have displaceable switching magnets, which can be guided within cylindrical guides 74*a* to 74*d* for movement up to and away from valve bodies 72, in order to displace the valve bodies 72 within fluid line assembly 70 by adjusting the magnetic field acting locally on them. FIG. 3 shows a ferromagnetic valve body 72 on connector formation 36 of cell culture container 12. The two valve bodies shown in FIG. 2 with four coupling formations 30*a* to 30*d* are sufficient to hold two coupling formations and thus the fluid line sections that penetrate them perpetually in fluidic communication, while the remaining two coupling formations for a fluid line are blocked. In the absence of a magnetic field of switching magnets, valve bodies 72 are prestressed into their respective closed positions by means of magnets 73*a* to 73*d* in the valve seats.

Fluid line 58 may be coupled to a waste disposal container, for example, and fluid line 60 may be coupled to a storage container for cleaning fluid.

Fluid channel ports 22, 28 and the fluid channel ports that are not provided with reference symbols in FIGS. 1 and 3 may be coupled to different storage containers for media, for example, to a storage container for nutrient medium, to a storage container for medium for removing adherent cells from inner surfaces of the cell culture container, and the like.

FIGS. 4 to 6 show a second embodiment of a fluid supply interface of the present invention. This second embodiment will be explained below only in so far as it differs from the first embodiment described above, the description of which is otherwise expressly referenced for explanation of the second embodiment.

Identical and functionally identical components and component sections are labeled with the same reference symbols as in FIGS. 1 to 3 of the first embodiment, but increased by the number 100.

One significant difference between the first and second embodiments is that the second embodiment has a fluid base 116 that can be displaced translationally relative to line component 114 along selection path A. On said fluid base, five fluid channel base connecting ports 122, 128, etc. are provided, for example, arranged in succession along selection path A. In the example shown, outermost connecting port 122 is selected as coupling connector formation 118 with fluid channel base connector formation 118. A power unit 165 (see FIG. 4) ensures a motorized adjustability of coupling connector formation 118 between the coupling position shown in FIG. 5 and a coupling ready position, in which the remaining four fluid channel base connector formations 119 of fluid channel base 116 are situated in FIG. 5.

Since the coupling connector formation is always located at the same point relative to line component 114, power unit 165 can be provided immovably relative to line component 114. It can have a pivot arm, for example, that is pivotable between an engaged position and a disengaged position and that can engage at one end with a fluid channel base connecting port 122 of the fluid channel base connector formation 118 selected as coupling connector formation 118 and, once it is engaged, can be displaced along coupling path K together with the engaged coupling connector formation.

A movement drive for the displacement of fluid channel base 116 relative to line component 114 along selection path A is not shown in FIGS. 4 to 6.

Another difference between the first and second embodiments involves the configuration of fluid line assembly 170. In the second embodiment, said assembly is configured as ring-shaped, i.e. the individual fluid line sections 170a to 170d that penetrate coupling formations 130a to 130d are connected to one another in series. The component part of line component 114 that carries line assembly 170 is shown enlarged in FIG. 6.

While in FIG. 5 the individual line sections are configured as substantially rectilinear between the individual coupling formations, in FIG. 6 the same line sections are configured as arcuate, curved about a central curvature axis X, which is orthogonal to the drawing plane of FIG. 6.

To receive valve body 172 after it has been lifted off of the respective valve seat, in the second embodiment, receiving recesses 180a to 180d are formed, which are configured as concave/partially spherical for suitably receiving the convex/spherical ball-shaped valve body 172. Receiving recesses 180a to 180d are offset orthogonally to the mouth opening surface of the associated coupling formations 130a to 130d (associated coupling formations and receiving recesses have the same lowercase letters) into the component part of line component 114 that carries the fluid line assembly. The mouth opening surfaces of individual coupling formations 130a to 130b extend substantially planar and orthogonally to the drawing plane of FIG. 4 and orthogonally to the respective penetration directions Da to Dd, along which a fluid channel section 132, 120, 154 and 156 penetrates the respective connector formations 118, 136, 140b and 140c.

Connector formations 118, 119, 136, 140b and 140c have seals 182a to 182d at their longitudinal ends that point toward line component 114, which seals are preferably embodied as integral with a conically shaped valve seat, on which valve ball 172 can rest when it seals the respective fluid channel section of the connector formation in question.

FIG. 7 shows a further embodiment of a component part of line component 214 that carries a valve line assembly 270.

Components and component sections that are identical or functionally identical to those of the second embodiment are provided with the same reference symbols in the embodiment of FIG. 7, but increased by the number 100.

Once again, the description of the preceding embodiments applies to the explanation of the embodiment of FIG. 7.

The embodiment of FIG. 7 differs from that of FIG. 6 substantially in that the connecting channels that connect the individual fluid line sections 270a to 270c to one another are configured as substantially rectilinear. In FIG. 7, fluid line assembly 270 is configured as polygonal but not as ring-shaped.

For the embodiment of FIG. 7 and that of FIG. 6, in contrast to the first embodiment, the fluid line sections that connect fluid line sections 170a to 170d and fluid line sections 270a to 207c, which penetrate the associated coupling formations 130a to 130d and 230a to 230c, respectively, are sized in terms of their cross-sectional dimensions such that valve body 170 and valve body 270, respectively, will not pass through and thus cannot travel from one coupling formation to another coupling formation.

In FIG. 7, connector formation 240c can be designed as a coupling connector formation of a fluid base, not shown, for example, and coupling formation 230c can be the switchable coupling formation.

The invention claimed is:

1. A fluid supply interface for a cell culture system for introducing a fluid into a cell culture container and/or for draining a fluid therefrom, comprising
a line component having
a first coupling formation for coupling of a first fluid channel,
a second coupling formation for coupling of a second fluid channel, and
a third coupling formation for coupling of a third fluid channel,
each of said coupling formations being penetrated by a fluid line section,
wherein the line component includes a fluid line assembly that selectively allows each fluid line section of the first, second and third coupling formations to be connected to each fluid line section of the other two coupling formations for the purpose of fluid transport,
wherein the fluid supply interface further includes a fluid channel base which is movable relative to the line component and which includes at least two fluid channel base connector formations, which are embodied as separate from one another and are connected to different fluid channels for the purpose of fluid transport, each of said fluid channel base connector formations being penetrated by a fluid channel section, and
wherein one of the three coupling formations is embodied as a switchable coupling formation for temporary production of a common fluid line segment with a fluid channel base connector formation, which is selected from among the fluid channel base connector formations by a relative movement between the line component and the fluid channel base.

2. The fluid supply interface according to claim 1, wherein the fluid channel base has at least two relative operating positions, in each of which the selected fluid channel base connector formation is selected as a coupling connector formation by being in closer proximity to the switchable coupling formation than others of the fluid channel base connector formations.

3. The fluid supply interface according to claim 2, wherein when the coupling connector formation is in closer proximity to the switchable coupling formation, the coupling connector formation is in a coupling ready position, in which the fluid channel section that penetrates the coupling connector formation and the fluid line section that penetrates the switchable coupling formation are aligned with one another, or in that when the coupling connector formation is in closer proximity to the switchable coupling formation the coupling connector formation is in a coupling position, in which the fluid channel section that penetrates the coupling connector formation and the fluid line section that penetrates the switchable coupling formation are coupled to form the common fluid line segment that penetrates the coupling connector formation and the switchable coupling formation.

4. The fluid supply interface according to claim 3, wherein the coupling connector formation is configured to be displaced between the coupling ready position and the coupling position without changing a relative position between the fluid channel base and the line component.

5. The fluid supply interface according to claim 4,
wherein the coupling connector formation is configured to be displaced relative to the fluid channel base between the coupling ready position and the coupling position along a coupling path, and is configured to be moved together with the fluid channel base relative to the line component along a selection path defined by a guide means,
wherein coupling path and selection path are different and are preferably orthogonal to one another.

6. The fluid supply interface according to claim 4, further comprising a power unit for displacing the coupling connector formation from the coupling ready position to the coupling position.

7. The fluid supply interface according to claim 1,
wherein the fluid line assembly connects the fluid line sections of the first, second, and third coupling formations of the line component to one another in parallel or in series,
wherein the parallel connection is configured as radial and the series connection is configured as arcuate or polygonal in the line component.

8. The fluid supply interface according to claim 1 wherein the fluid line assembly includes a receiving recess in a region of at least one coupling formation offset into the line component in a direction orthogonal to the opening surface of a mouth of the fluid line section that penetrates the coupling formation in the at least one coupling formation, said receiving recess being configured for temporary accommodation of a valve body and being configured as at least partially complementary to a section of the surface of the valve body.

9. The fluid supply interface according to claim 1, wherein a mouth of the fluid line section at the switchable coupling formation is encompassed by a seal or by a contact surface, which is configured for attachment thereon of a seal that is provided on each of the fluid channel base connector formations.

10. The fluid supply interface according to claim 1, wherein at least one of the coupling formations is permanently coupled to a fluid channel connector formation to form a second common fluid line segment that penetrates the fluid channel connector formation and the at least one of the coupling formations.

11. The fluid supply interface according to claim 1, wherein each of the coupling formations has a valve seat and a valve body, which rests on the valve seat in an operating mode in which a respective coupling formation is blocked for fluid passage.

12. The fluid supply interface according to claim 11, wherein the valve body is made at least partially of ferromagnetic material, and in that the valve seat has a magnet, which magnet magnetically prestresses the valve body into a closed position, in which the valve body rests on the valve seat.

13. The fluid supply interface according to claim 11, wherein at least one displacement section of the fluid line assembly that proceeds from each of the coupling formations and extends toward a further one of the coupling formations is dimensioned such that the at least one displacement section permits a displacement of the valve body away from the respective coupling formation and back.

14. The fluid supply interface according to any of claim 11, wherein the valve body includes ferromagnetic material, and in that the fluid supply interface has a magnetic switching device with magnetic field strengths that are configured to be adjusted locally at the coupling formations, and with which the valve body can be released from the valve seat.

15. The fluid supply interface according to claim 1, wherein the fluid channel base is rotatable relative to the line component about a rotational axis which is parallel to the orientation of the fluid line section that penetrates the switchable coupling formation, or is displaceable relative to the line component along a translational axis, which is orthogonal to the orientation of the fluid line section that penetrates the switchable coupling formation.

16. A cell culture system having at least one cell culture container, at least two separate fluid reservoirs, a fluid disposal sink and a fluid supply interface according to claim 1,
wherein the cell culture container includes a connector formation,
wherein the fluid channel base connector formations are fluidically connected to the fluid reservoirs,
wherein the first coupling formation of the line component is configured to produce a temporary fluid transport connection with the cell culture container connector formation, the second coupling formation of the line component is configured as the switchable coupling formation for producing a temporary fluid transport connection with one of the fluid channel base connector formations and the third coupling formation of the line component is configured to produce a temporary or permanent fluid transport connection with the fluid disposal sink.

\* \* \* \* \*